Figure 2:
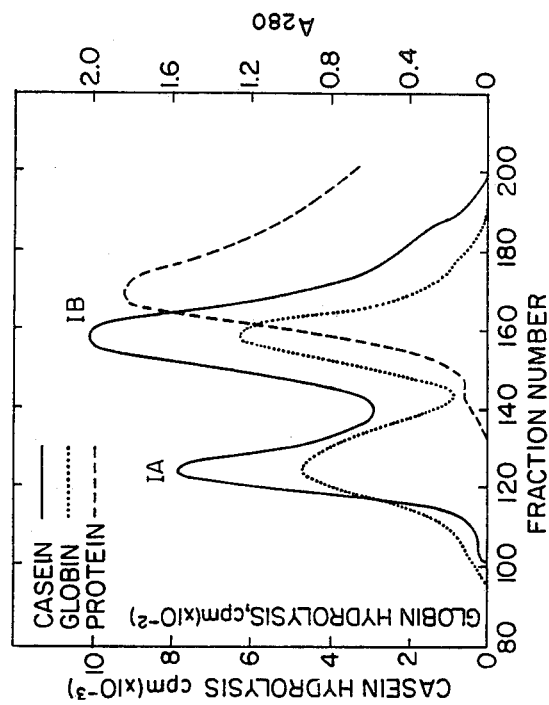

United States Patent [19]

Goldberg et al.

[11] 4,390,629

[45] Jun. 28, 1983

[54] POLYPEPTIDE DEGRADING ENZYMES

[75] Inventors: Alfred L. Goldberg, Brookline; K. H. Sreedhara Swamy, Allston; Chin H. Chung, Chestnut Hill, all of Mass.

[73] Assignee: President and Fellows of Harvard College, Cambridge, Mass.

[21] Appl. No.: 249,104

[22] Filed: Mar. 30, 1981

[51] Int. Cl.³ .................. C12N 9/52; C12N 9/48; C12R 1/19; C12R 1/42
[52] U.S. Cl. .................. 435/220; 435/212; 435/814; 435/815; 435/822; 435/849; 435/879
[58] Field of Search ............... 435/220, 212, 814, 815, 435/849, 829

[56] References Cited

FOREIGN PATENT DOCUMENTS 141323  4/1980  German Democratic Rep. .................. 435/220

OTHER PUBLICATIONS

Pacaud et al. (1971), *Eur. J. Biochem.* 23, 435–442.
Pacaud et al. (1975), *J. Biol. Chem.* 250, 7771–7779.
Pacaud et al. (1976), *Eur. J. Biochem.* 69, 141–151.
Miller et al. (1976), *J. Bacteriol.* 127, 490–497.
Heiman et al. (1978), *J. Bacteriol.* 135, 588–594.
Kowit et al. (1976), *J. Bacteriol.* 128, 776–784.
Regnier et al. (1975), *Eur. J. Biochem.* 54, 445–451.
Lazdunski et al. (1975), *Eur. J. Biochem.* 60, 363–369.
Cheng et al. (1979), *J. Biol. Chem.* 254, 4698–4706.
Miller (1975), *Ann. Rev. Microbiol.* 29, 485–504.
Miller, *Limited Proteolysis in Microorganisms,* Cohen et al., eds., pp. 65–68 (HEW Pub. No. (NIH) 79-1591).

*Primary Examiner*—Lionel M. Shapiro

[57] ABSTRACT

Proteases derived from *E. coli,* and a method for preparing a proteinaceous mixture having proteolytic activity.

2 Claims, 2 Drawing Figures

POLYPEPTIDE DEGRADING ENZYMES

The invention described herein was made in part in the course of work under grants from the National Institutes of Health and the Juvenile Diabetes Foundation.

This invention relates to proteolytic enzymes from bacteria.

Proteolytic enzymes are currently widely used in industry and medicine. For example, they can be used as additives in preparing laundry detergents, as catalysts in the drug and chemical industries, as reagents in converting starch to soluble sugars, in converting waste protein to useful alternative chemicals, in generating polypeptides from cloned precursors, in destruction of waste-products, and in dissolution of blood clots. As more proteolytic enzymes are isolated, additional uses for them will undoubtedly be found.

Several attempts have been made to isolate and purify proteolytic enzymes of *E. coli*. "Protease I", described in Pacaud et al. (1971), *Eur. J. Biochem.* 23, 435, and "Protease II", described in Pacaud et al. (1975), *J. Biol. Chem.* 250, 7771 were identified by their ability to cleave chromogenic amino acid esters. However, these enzymes, when purified, showed very little or no activity against protein substrates; Pacaud et al. (1976), *Eur. J. Biochem.* 69, 141; Kowit et al. (1976), *J. Bacteriol*, 128, 776. Furthermore, it has been observed that mutants of *E. coli* and *Salmonella typhymurium* lacking these two enzymes have normal capacities for carrying out both early and late steps in intracellular protein gradation; Miller et al. (1976), *J. Bacteriol.* 127, 490; Heiman et al. (1978), *J. Bacteriol.* 135, 588; Kowit et al. (1976), *J. Bacteriol.* 128, 776.

In addition, the partial purification of "protease A", which is said to be active against casein, has been described in Regnier et al. (1975), *Eur. J. Biochem.* 54, 445, and amino-peptidase, said also to have endopeptidase activity, is described in Lazdunski et al. (1975), *Eur. J. Biochem.* 60, 363, although this latter claim has not been supported by further work (Swamy, Chin, Goldberg; unpublished observation). And in Cheng et al. (1979), *J. Biol. Chem.* 254, 4698, there is described an enzyme from *E. coli*, "protease III", which hydrolyzes incomplete fragments of β-galactosidase in vitro.

Finally, Miller (1975), *Ann. Rev. Microbiol.* 29, 485 and Miller in *Limited Proteolysis in Microorganisms,* Cohen et al., eds., 65 (HEW Pub. No. (NIH) 79-1591) describe several enzymes which cleave small peptide substrates; these enzymes are apparently involved in the final exoproteolytic reactions that convert peptides to free amino acids.

We have now isolated, purified, and characterized seven distinct proteolytic enzymes of *E. coli*. These newly discovered and isolated enzymes have a wide variety of uses as outlined above and have the additional advantage of being readily available because of the increasingly widespread use of *E. coli* for other commercial purposes; e.g., as a source for other enzymes and as the producer of cloned hormones and other polypeptides.

Six of the enzymes of the invention are capable of degrading large protein substrates including [$^{14}$C] methyl-globin and [$^3$H] methyl-casein. We have named these enzymes Do, Re, Mi, Fa, So, and La. The seventh enzyme of the invention, which is of cytoplasmic origin, degrades insulin, and has thus been named Ci. We have characterized all seven of the enzymes of the invention; their properties are described below.

The enzymes of the invention are all present in *E. coli* in proportionally minute amounts. As prepared by the methods described below, all except Protease La are purified to near homogeneity. The only contaminants possibly present in these preparations are proteins which lack any proteolytic activity.

In another aspect, the invention features a proteinaceous mixture having proteolytic activity, and a simple method for preparing the mixture. The method includes breaking open cells of *E. coli* (or any *Salmonella* or *Shigella* species or of related, enteric, gram-negative bacteria), removing the insoluble cellular components from the resulting homogenate, fractionating the solubilized protein extract, and isolating the fraction exhibiting proteolytic activity. This fraction, a concentrate containing several proteolytic enzymes, is useful for a variety of purposes, and is particularly valuable because some proteolytic enzymes in the concentrate act synergistically.

Although rupturing in a French press is preferred, any method of breaking open the bacterial cells can be used, e.g., sonication or lysis using a suitable chemical agent. Also, although fractionating is preferably carried out using a DEAE-cellulose column and gel chromatography, any alternative method for fractionating proteins on the basis of charge (e.g., other ion-exchange columns or isoelectric focusing) or size (e.g., other gel chromatography columns) or solubility (e.g., ph precipitation or ammonium sulfate precipitation) can be used. *E. coli* is the preferred source of the proteolytic mixture, but any closely related species of bacteria (e.g., species of Salmonella, Shigella or other enteric gram-negative genera) can be used.

Figure 1:
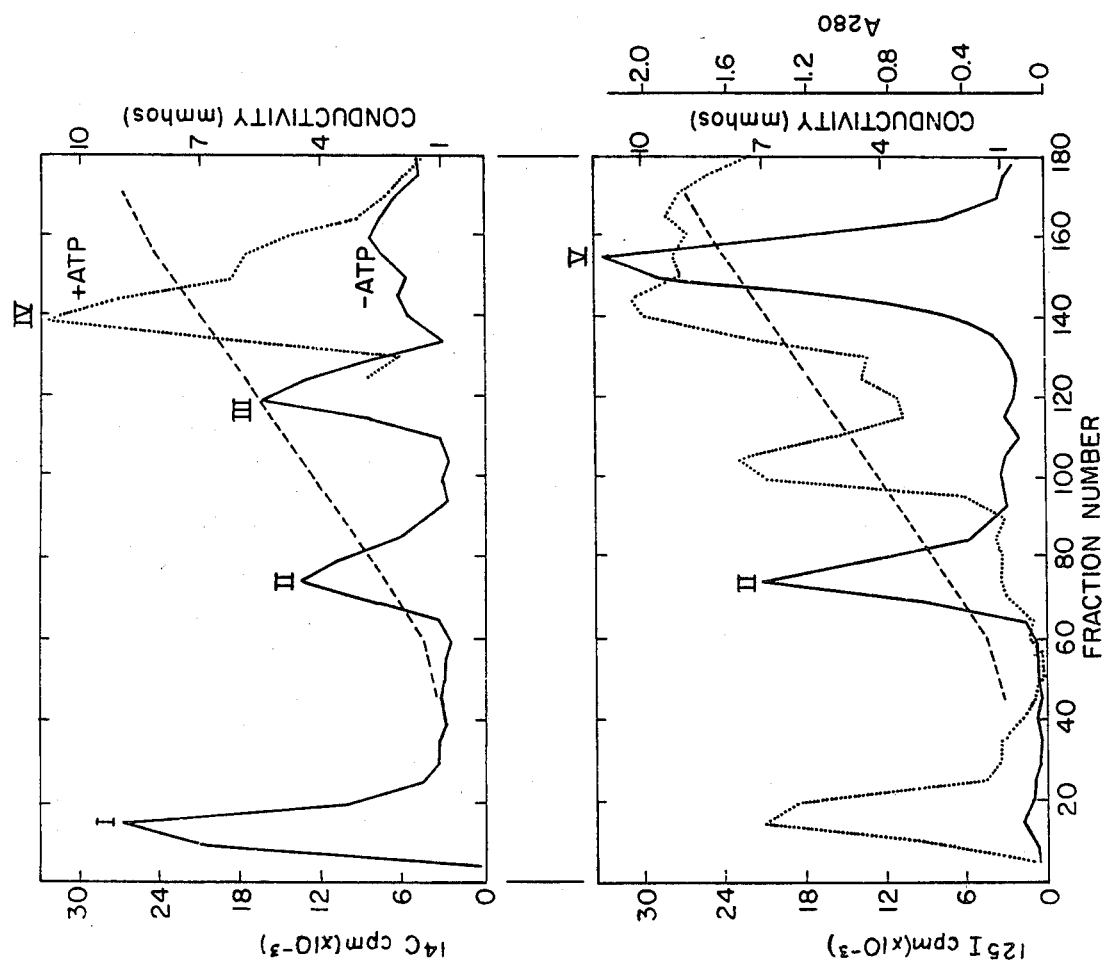

In the drawings,

FIG. 1 is a pair of graphs showing the relationship between the DEAE-cellulose chromatographic profile of *E. coli* cell-free extract and globin-degrading activity (top graph) and insulin-degrading activity (bottom graph). The top graph shows conductivity (dashed line) and activity in the presence of ATP (dotted line) and absence of ATP (solid line). The bottom graph shows conductivity (dashed line), absorbance at $A_{280}$ (dotted line), and activity (solid line).

FIG. 2 is a graph illustrating the Sepharose 6B gel filtration profile of peak I of FIG. 1.

The following specific examples are intended to more particularly point out the invention, without acting as limitations upon its scope.

Example 1 refers to a variety of buffers, for convenience designated Buffers A-O. Their compositions are given below:

Buffer A: 50 mM Tris-HCl, pH 7.8, 10 mM MgCl$_2$, 200 mM KCl

Buffer B: 10 mM Tris-HCl, pH 7.8, 5 mM MgCl$_2$

Buffer C: 50 mM Tris-HCl, pH 7.8, 10 mM MgCl$_2$

Buffer D: 50 mM Tris-HCl, pH 7.8, 5 mM MgCl$_2$, 100 mM NaCl

Buffer E: 10 mM Sodium acetate, pH 5.6

Buffer E: 10 mM Tris-HCl, pH 8.4

Buffer G: 25 mM Tris-HCl, pH 7.8, 5 mM MgCl$_2$, 50 mM NaCl

Buffer H: 10 mM Sodium acetate, pH 5.2, 2.5 mM MgCl$_2$

Buffer I: 50 mM Tris-HCl, pH 7.8, 5 mM MgCl$_2$, 50 mM NaCl

Buffer J: 10 mM Sodium acetate, pH 5.0, 2.5 mM MgCl$_2$
Buffer K: 10 mM Tris-HCl, pH 8.4, 1 mM cystein, 20 mM NaCl, 5 mM MgCl$_2$
Buffer L: 10 mM Tris-HCl, pH 8.0, 5 mM MgCl$_2$, 10 mM mercaptoethanol
Buffer M: 10 mM Tris-HCl, pH 7.8, 5 mM MgCl$_2$, 100 mM NaCl
Buffer N: 10 mM Tris-HCl, pH 7.8
Buffer O: 10 mM Potassium phosphate, pH 6.5

The examples also refer to proteolytic activities. These were determined using the substrates [$^{14}$C] globin and [$^3$H] casein. To obtain these substrates, crystalline beef hemoglobin (Sigma) was methylated with [$^{14}$C] formaldehyde (40–60 mCi/mmole, New England Nuclear) and bovine α-casein with [$^3$H] formaldehyde (85 mCi/mmole, New England Nuclear) according to the procedure of Rice and Means (J. Biol. Chem. 246, 831–832, 1971). To increase its proteolytic susceptibility, heme was extracted from the hemoglobin by use of methylethylketone (Teale, *Biochim. Biophys. Acta* 35, 543, 1959). The specific activity of [$^{14}$C] globin was about 2–4×10$^6$ cpm/mg, while that of [$^3$H] casein was 2–3×10$^7$ cpm/mg.

Proteolytic activity was estimated by following the degradation of [$^{14}$C] globin, [$^3$H] casein or [$^{125}$I] insulin (125–140 mCi/mg, Cambridge Nuclear and Radiopharmaceutical Corporation, Billerica, MA) to products soluble in 10% trichloroacetic acid. Unless otherwise indicated, all the assays were carried out in buffer C in the presence and absence of 3 mM ATP. When assayed with globin or casein as substrates, each incubation mixture contained an appropriate amount of enzyme preparation of 4–5 μg of [$^{14}$C] globin or 10–15 μg of [$^3$H] casein in a final volume of 0.5 ml. Assays using insulin as a substrate contained 12.5 μg insulin (Eli Lilly Co., Indianapolis, Ind.), a trace amount of [$^{125}$I] insulin (about 12–15,000 cpm), 0.125% bovine serum albumin, and the enzyme preparation in a final volume of 0.5 ml. The incubations were performed for two hours at 30° C. when globin or casein were the substrates, and for one hour at 37° C. when insulin was the substrate. Each reaction was stopped by the addition of 60 μl of 100% TCA and 40 μl of bovine serum albumin (30 mg/ml) as a carrier. The assay tubes were kept on ice for 30 min, and after centrifugation, 0.4 ml of acid soluble products from [$^{14}$C] globin hydrolysis were counted in 4 ml of Liquiscint (National Diagnostics, Parsippany, N.J.). The products of [$^{125}$I] insulin hydrolysis were counted in an auto gamma spectrometer.

Protein determinations were made by the method of Lowry et al. (1951) using crystalline bovine serum albumin as standard.

EXAMPLE 1

Protease Purification

Preparation of Cell-free Extract

The cell-free extract containing all seven proteolytic enzymes of the invention, in unpurified form, was prepared from frozen *E. coli* K12 cells (such cells may be grown fresh or purchased in large amounts from Grain Processing Co., Muscatine, Iowa). Seventy-five grams of frozen cells were thawed at 4° C., and the thawed cells suspended in 150 ml of buffer A. The cell suspension was then disrupted in a French press at 12,000 psi, the resulting homogenate was centrifuged at 30,000 xg for 30 min., and the supernatant was then spun again in a Beckman ultracentrifuge at 130,000 xg for three hours. Following extensive dialysis against buffer B, the insoluble material was removed from the supernatant by centrifugation. Seventy-five grams of cells (wet weight) yielded 3 to 3.5 g of protein in the soluble fraction (130,000 xg supernatant).

Fractionation of Cell-free Extract on DEAE-cellulose

The dialyzed cell-free extract (3.0 g protein) was applied to a DEAE-cellulose column, 2.5×27 cm, equilibrated with buffer B. The column was washed with the same buffer until the A$_{280}$ of the eluate was less than 0.05. The adsorbed proteins were then eluted with 1500 ml of a linear salt gradient (0–0.2 M NaCl). The flow rate was 100 ml per hour and 15 ml fractions were collected. Alternate fractions were assayed for proteolytic activity against [$^{14}$C] globin and [$^{125}$I] insulin in the presence and absence of 3 mM ATP. As is shown in FIG. 1, five different peaks of proteolytic activity against three substrates were found. For convenience, they were designated peaks I–V, according to their order of elution from the column. All the globin-hydrolyzing peaks also hydrolyzed $^3$H-casein and are much more active against this substrate than against $^{14}$C-globin. The globin-degrading activity in peak IV, but in no other peak, was stimulated dramatically (4–20 fold) by ATP. Since protein breakdown in intact cells requires ATP (Goldberg, A. L. and St. John, A. C. (1976), Ann. Rev. Biochem. 45, 747–803; Olden, K. and Goldberg, A. L., Biochim. Biophys. Acta 542: 385 (1978)), the enzyme in peak IV probably is the rate limiting enzyme for intracellular protein degradation (Murakami, K., Voellmy, R. and Goldberg, A. L., J. Biol. Chem. 254: 8194 (1979)).

The purification steps described below for individual enzymes correspond to an initial enzyme preparation (i.e., the DEAE-cellulose step) from 250–300 g of cells. This amount has been found useful for further purification and may be obtained by combining peaks (from the DEAE-cellulose column) from several different preparations.

Proteases in Peak I—Do and Re

Peak I (i.e., the fractions that did not adsorb to DEAE-cellulose) showed strong hydrolytic activity against globin and casein. To resolve this activity further, fractions under peak I were pooled and concentrated by precipitating the proteins by adding solid ammonium sulfate to 95% saturation. After centrifugation at 31,000 xg for 30 min., the pellet was dissolved in buffer D and then dialyzed against the same buffer. After removing the insoluble material by centrifugation, the protein (7.5 ml) was loaded on a Sepharose 6B column (2.5×110 cm) equilibrated with buffer D. The flow rate was 25 ml per hour and 4.0 ml fractions were collected. Fractions were assayed in 50 mM Tris-HCl, pH 7.8. As is shown in FIG. 2, gel filtration resolved peak I into two distinct peaks, referred to as proteases Do (IA) and Re (IB). Both peaks hydrolyze globin and casein.

The active fractions (peak IA) corresponding to protease Do from the Sepharose 6B column were pooled, concentrated by ultrafiltration through PM 10 membrane and stored at −30° C.

Properties of Do

Protease Do is located primarily in the cytoplasm with about 15% of its activity detectable in the periplasm. The enzyme has an unusually large molecular weight of about 520,000 daltons, as determined by gel filtration on Sepharose 6B.

The enzyme is very sensitive to diisopropyl fluorophosphate, and therefore is a serine protease. It is not sensitive to metal chelators or sulfhydryl inhibitors.

Purification of Protease Re (Peak IB)

Since protease Re is much more active against casein than globin, all further purification and characterizations were carried out using casein..

Peak IB fractions exhibiting protease activity were combined, and proteins were precipitated by adding solid ammonium sulfate to 55% saturation. After centrifugation at 42,000 xg for 30 min., the pellet was discarded and the supernatant was brought to 80% saturation with ammonium sulfate. After stirring the suspension for 2 hrs. at 4° C., the precipitated proteins were collected by centrifugation at 31,000 xg for 30 min., resuspended in buffer E, and dialyzed against the same buffer overnight. The proteins precipitated at pH 5.5 were discarded by centrifugation at 42,000 xg for 30 min. and the supernatant was applied to a CM-cellulose column (1.5×16 cm) that had been equilibrated with buffer E. The flow rate was adjusted to 50 ml per hour and 3 ml fractions were collected. After washing the column with the buffer, adsorbed protein was eluted with buffer E containing a linear gradient of 0 to 0.2 M NaCl. The peak of the protease Re activity eluted at about 0.15 M salt concentration.

The active fractions from the last step were pooled, concentrated, dialyzed against buffer I, and applied to an Ultrogel AcA44 column (1.5×95 cm) equilibrated with buffer I. Two-ml fractions were collected at a flow rate of 20 ml per hour. The active fractions from the Ultrogel column were then pooled, dialyzed against buffer F, and loaded on a DEAE-Sepharose column (0.5×9.5 cm) equilibrated with the same buffer. Protein was eluted with buffer F containing a linear gradient of 0 to 0.2 M NaCl at a flow rate of 20 ml per hour, and 3 ml fractions were collected. The peak of enzyme activity was observed at about 0.075 M NaCl concentration.

Properties of Re

Protease Re hydrolyzes globin and casein. In the intact cell, the enzyme is almost equally distributed between periplasm and cytoplasm.

The enzyme has a molecular weight of about 68,000 daltons as determined by gel filtration on Sephadex G-75. Analysis of the enzyme on SDS-polyacrylamide gel electrophoresis showed a single band of 68,000 daltons, suggesting that the enzyme is composed of a single polypeptide chain.

The enzyme is active over the pH range of 7 to 8.5, with the optimum activity at pH 8.0. The enzyme is sensitive to diisopropyl fluorophosphate and phenylmethyl sulfonyl fluoride; therefore, it also is a serine protease. It is also sensitive to metal chelating agents such as EDTA and o-phenanthroline.

Proteases in Peak II—Pi, Mi and Fa

Peak II from the DEAE-cellulose column contains three enzymes which can be resolved by CM-cellulose chromatography. These enzymes can also be separated on an isoelectric focusing column.

The pooled peak II fraction from the DEAE-cellulose column was concentrated by ultrafiltration through PM10 membrane, dialyzed against buffer H and loaded onto a CM-cellulose column (1.5×16 cm) equilibrated with the same buffer. After washing the column with 100 ml of buffer, the protein was eluted with a 0 to 0.3 M NaCl linear gradient (350 ml total volume). The flow rate was 45 ml per hr. and 3 ml fractions were collected. Alternate fractions were assayed against $^3$H-casein, $^{14}$C-globin and $^{125}$I insulin. One of the three peaks of proteolytic activity hydrolyzed insulin, but not casein or globin, while the other two degraded casein and globin, but not insulin. The insulin-degrading activity, we have named Pi (periplasmic insulin-degrading enzyme) because we found that it is localized exclusively in the periplasmic space. It corresponds to the protease III described in Cheng et al., Id. (1979). The two casein-degrading enzymes we have named Mi and Fa.

The active fractions under each peak were pooled, concentrated by ultrafiltration through PM10 membrane, and dialyzed against buffer C. The resulting concentrates constituted, respectively, samples of Pi, Mi and Fa in solution with buffer.

Properties of Mi and Fa

Both enzymes degrade globin and casein and have molecular weights of 110,000 daltons as determined by gel filtration on Sephadex G-200. Mi is periplasmic and Fa is cytoplasmic. The isoelectric points of Mi and Fa are 6.75 and 7.4, respectively.

Both Mi and Fa are serine proteases, although Fa is inhibited more strongly than Mi by diisopropyl fluorophosphate. EDTA inhibits Mi by about 35% and Fa by 60%. Both enzymes are about 35% inhibited by o-phenanthroline and are substantially unaffected by sulfhydryl inhibitors. Experiments carried out using $^{14}$C globin as a substrate showed that, after incubation at 50° C. for 15 min., Mi lost more than 90% of its activity, while Fa remained completely stable.

Peak III—So

The casein-hydrolyzing activity of peak III from the DEAE-cellulose column was pooled, and solid ammonium sulfate was slowly added to 45% saturation with stirring at 4° C. After additional stirring for 1 hr, the suspension was centrifuged at 42,000 xg for 30 min, and the pellet was discarded. Ammonium sulfate was again added to the supernatant to 75% saturation and the mixture was then stirred at 4° C. for 2 hr. The pellet was collected by centrifugation at 42,000 xg for 30 min, dissolved in buffer I, and then dialyzed overnight against the same buffer.

The dialyzed material was applied to an Ultrogel AcA34 column (2.5×110 cm) equilibrated with buffer I. Protein was eluted with buffer I at a flow rate of 20 ml per hour and fractions of 3 ml were collected. The fractions containing protease activity were pooled and dialyzed against buffer J at 4° C. overnight. Insoluble proteins were removed by centrifugation at 42,000 xg for 30 min.

The supernatant was loaded on a CM-cellulose column (1.5×12.0 cm) which had been equilibrated with buffer J. Protein was eluted with a linear gradient of 0 to 0.3 M NaCl in buffer J. Fractions of 3 ml were collected at a flow rate of 30 ml per hour. Fractions with high protease activity were pooled, concentrated, and dialyzed against buffer K at 4° C. for 8 hr.

The dialyzed protease preparation from the previous step was then applied to a DEAE-Sepharose column (1.5×5.6 cm) equilibrated with buffer K. Protein was eluted with buffer K at a flow rate of 12 ml per hour and fractions of 3 ml were collected. Protease So activity was eluted in the flow-through fractions, while most of the non-enzymatic proteins were bound to CM-cellulose. The active fractions, when pooled and concentrated, constituted a sample of the proteolytic enzyme So which was purified about 2,000-fold from the initial DEAE-cellulose step.

Properties of So

Protease So, a cytoplasmic enzyme, has a molecular weight of 140,000 daltons as determined by gel filtration on Sephadex G-200. On SDS-polyacrylamide gel electrophoresis, the enzyme showed a single band of 70,000 daltons, suggesting that the native enzyme is a dimer of identical subunits. The enzyme is homogeneous as determined by polyacrylamide gel electrophoresis under denaturing and non-denaturing conditions. It is active over a pH range of 6 to 8, with maximum activity at a pH of 6.5. It is sensitive to diisopropyl fluorophosphate and phenylmethyl sulfonyl fluoride, indicating that it is a serine protease. It is also about 80% inhibited by pentamidine (1 mM). It is not sensitive to metal chelating agents or sulfhydryl inhibitors.

Peak IV—La

The enzyme in peak IV eluted from the DEAE-cellulose column between 0.105 and 0.15 M NaCl. The fraction with high ATP-dependent globin (or casein) degrading activity was pooled, dialyzed against buffer L and loaded onto a DEAE-Sepharose column (1.5×30 cm) equilibrated with buffer L. The proteins were eluted with a 0–0.2 M NaCl gradient in buffer L. The protease activity was eluted at about 0.12 M NaCl concentration. Fractions with highest activity were pooled and stored at −30° C.

Properties of La

The degradation of globin and casein by La was increased 2.5 to 20-fold by the presence of 3 mM ATP. This effect requires the presence of $Mg^{++}$ ions. Other nucleotide triphosphate (CTP and UTP or deoxyadenosine triphosphate) also stimulate but less effectively. Nonmetabolizable analogs of ATP do not stimulate proteolysis as does ATP.

The molecular weight of the enzyme was estimated by sucrose density gradient centrifugation and by Sephadex G-200 gel filtration to be about 115,000 daltons. It is present in the cytoplasm of the cell and is sensitive to diisopropyl fluorophosphate and phenylmethyl sulfonyl fluoride, indicating that it is a serine protease. It is also inhibited by the sulfhydryl group blocking reagent, N-ethyl maleimide. The enzyme is also sensitive to inhibition by Vanadate, a potent inhibitor of ATPases; therefore, ATP cleavage is probably essential for La's proteolytic activity; this property differentiates La from any proteolytic enzyme previously purified from bacterial or animal cells.

Peak V—Ci

The insulin-degrading activity of peak V from the DEAE-cellulose column was pooled and dialyzed against buffer E at 4° C. overnight. Insoluble proteins were removed by centrifugation at 42,000 xg for 30 min. The supernatant fraction was adjusted to pH 7.8 by adding 200 mM Tris-HCl, pH 8.0, and solid ammonium sulfate was then added to 40% saturation, and it was stirred for 2 hrs. at 4° C. The suspension was centrifuged at 31,000 xg for 30 min. and the pellet was discarded. The supernatant was then brought to 65% saturation with ammonium sulfate and stirred for 2 hrs. at 4° C. The pellet was collected by centrifugation at 31,000 xg for 30 min., dissolved in buffer M, and dialyzed against the same buffer.

The dialyzed material was next applied to an Ultrogel AcA 34 column (2.5×105 cm) equilibrated with buffer M. Protein was eluted with the same buffer, and 3 ml fractions were collected at a flow rate of 20 ml per hr.

The active fractions from the Ultrogel column were pooled, dialyzed against buffer N overnight at 4° C., and applied to a butyl agarose column (1.0×18 cm) that had been equilibrated with the same buffer. Protein was eluted by a linear gradient of 0 to 0.2 M NaCl in buffer N and 3 ml fractions were collected at a flow rate of 30 ml per hr. The peak of enzyme activity appeared at a NaCl concentration of about 0.08 M.

The fractions containing insulin-degrading activity from the butyl agarose column were pooled, dialyzed against buffer 0 at 4° C. overnight, and loaded on a hydroxyapatite column (1.0×8.5 cm) equilibrated with the same buffer. After washing the column with the same buffer, protein was eluted with a linear gradient of 10 to 200 mM potassium phosphate, pH 6.5. Two ml fractions were collected at a flow rate of 20 ml per hr. The active fractions from the column were pooled and dialyzed against buffer N.

Properties of Ci

Protease Ci has a molecular weight of 125,000 daltons as determined by gel filtration on Sephadex G-200. The enzyme is located in cytoplasm of the cell and has a sharp pH optimum at 7.5. The enzyme activity is inhibited by the metal chelating agent, o-phenanthroline, but not by EDTA or EGTA. The enzyme is also sensitive to the sulfhydryl inhibitor, p-hydroxymercuribenzoate. The antibiotics bacitracin and globomycin also strongly inhibit the protease activity at concentrations of 5–20 μg per ml. The enzyme's activity is markedly stimulated by various divalent cations, particularly by $Mn^{++}$ and $Co^{++}$, but not by $Zn^{++}$.

EXAMPLE 2

Rapid Isolation of a Highly Active Proteolytic Fraction From *E. coli*

A highly active proteolytic fraction containing proteases Do, Re, Me, Fa and Pi was isolated from *E. coli* by a single step using DEAE-cellulose chromatography. A crude cell-free extract was prepared as described above and dialyzed extensively against 10 mM Tris-HCl, pH 7.8, 5 mM $MgCl_2$ and 50 mm NaCl. After removing the insoluble materials by centrifugation, the extract was applied to a DEAE-cellulose column (4×52 cm) equilibrated with the dialysis buffer. The column was washed with two bed volumes of the same buffer. The flow rate was 100 ml per hour and 15 ml fractions collected. Alternate fractions were assayed for proteolytic activity against [$^{14}C$] globin (or [$^3H$] casein) and [$^{125}I$] insulin as described above. The proteolytic fraction thus isolated had high specific activity and was found to contain about 8–10% of the proteins applied to the column.

The general method can be used to easily prepare a protease-rich extract from *E. coli* or from any Salmonella or Shigella culture. The method is particularly valuable for *E. coli* because of the increasing industrial use this species is likely to see in the near future.

What is claimed is:

1. A method of preparing a proteinaceous mixture having proteolytic activity and containing proteases Do, Re, Mi, Fa, and Pi, said method comprising providing a culture of cells of *E. coli* or a species of Salmonella or Shigella, breaking open said bacterial cells to form a cell homogenate, removing water-insoluble cellular components from said homogenate to form an extract containing solubilized protein, fractionating the protein of said extract, and isolating said fraction exhibiting proteolytic activity and containing protease, Do, Re, Mi, Fa, and Pi, said fraction comprising said proteinaceous mixture.

2. A proteinaceous mixture having proteolytic activity and containing protease Do, Re, Mi, Fa, and Pi, said mixture being prepared by the process of providing a culture of cells of *E. coli* or a species of Salmonella or Shigella, breaking open said bacterial cells to form a cell homogenate, removing water-insoluble cell components from said homogenate to form an extract containing solubilized protein, fractionating the protein of said extract, and isolating said fraction exhibiting proteolytic activity, said fraction comprising said proteinaceous mixture.

* * * * *